United States Patent
Morse et al.

(10) Patent No.: US 6,589,777 B1
(45) Date of Patent: Jul. 8, 2003

(54) STEREOSELECTIVE MICROBIAL REDUCTION OF A RACEMIC TETRALONE

(75) Inventors: Brook K. Morse, Colchester, CT (US); Susan J. Truesdell, Warwick, RI (US); John W. Wong, East Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/427,424

(22) Filed: Oct. 26, 1999

Related U.S. Application Data

(60) Provisional application No. 60/106,233, filed on Oct. 29, 1998.

(51) Int. Cl.[7] .................................................. C12P 7/26
(52) U.S. Cl. ..................... 435/280; 435/252.1; 435/170; 435/171; 435/254.01
(58) Field of Search .............................. 435/280, 254.1, 435/252.1, 170, 171

(56) References Cited

U.S. PATENT DOCUMENTS

| | | | |
|---|---|---|---|
| 4,536,518 A | 8/1985 | Welch, Jr. et al. | 514/647 |
| 4,777,288 A | 10/1988 | Quallich et al. | 562/491 |
| 4,839,104 A | 6/1989 | Quallich et al. | 260/396 |
| 4,855,500 A | 8/1989 | Spavins | 564/270 |
| 4,940,731 A | 7/1990 | Bick | 514/657 |
| 4,962,128 A | 10/1990 | Doogan et al. | 514/647 |
| 5,049,497 A | 9/1991 | Kluge et al. | 435/148 |
| 5,082,970 A | 1/1992 | Braish | 564/424 |
| 5,130,338 A | 7/1992 | Bacopoulos | 514/646 |
| 5,196,607 A | 3/1993 | Quallich | 568/327 |
| 5,248,699 A | 9/1993 | Sysko et al. | 514/647 |
| 5,442,116 A | 8/1995 | Welch et al. | 564/222 |
| 5,463,126 A | 10/1995 | Williams | 564/222 |
| 5,466,880 A | 11/1995 | Quallich | 568/319 |
| 5,523,223 A | 6/1996 | Kula | 435/189 |
| 5,580,764 A | 12/1996 | Holt et al. | 435/118 |
| 5,597,826 A | 1/1997 | Howard et al. | 514/255 |
| 5,618,707 A | 4/1997 | Homann | 435/146 |
| 5,750,794 A | 5/1998 | Quallich | 568/322 |

OTHER PUBLICATIONS

Bauer, A. et al. *Biotechnology Letters*, vol. 18(3), pp. 343–348 (1996).
Bortonlini, O. et al. *Tetrahedron: Asymmetry*, vol. 9, pp. 647–651 (1998).
Madyastha, K.M. et al. *Biochemical and Biophysical Research Communications*, vol. 211(2), pp. 540–546 (1995).
Nakamura, K. et al. *Tetrahedron Letters*, vol. 37(10), pp. 1629–1632 (1996).
Patel, R.N. et al. *Applied and Environmental Microbiology*, vol. 38(2), pp. 219–223 (1979).
Patel, R.N. et al. *Enzyme Microb. Technol.* vol. 13, pp. 906–912 (1991).
Patel, R.N. et al. *Enzyme Microb. Technol.*, vol. 14, pp. 778–784 (1992).

Trost, P. et al. *Eur. J. Biochem.* vol. 234, pp. 452–458 (1995).
Wada, M. et al. *Biosci. Biotechnol. Biochem.* vol. 62 (2), pp. 280–285 (1998).
Welch, W. M., Jr. et al. *Journal of Medicinal Chemistry*, vol. 27(11), pp. 1508 (1984).

*Primary Examiner*—Irene Marx
(74) *Attorney, Agent, or Firm*—Peter C. Richardson; Gregg C. Benson; Jennifer A. Kispert

(57) ABSTRACT

The present invention relates to processes for carrying out the following stereoselective microbial reduction of a racemic tetralone:

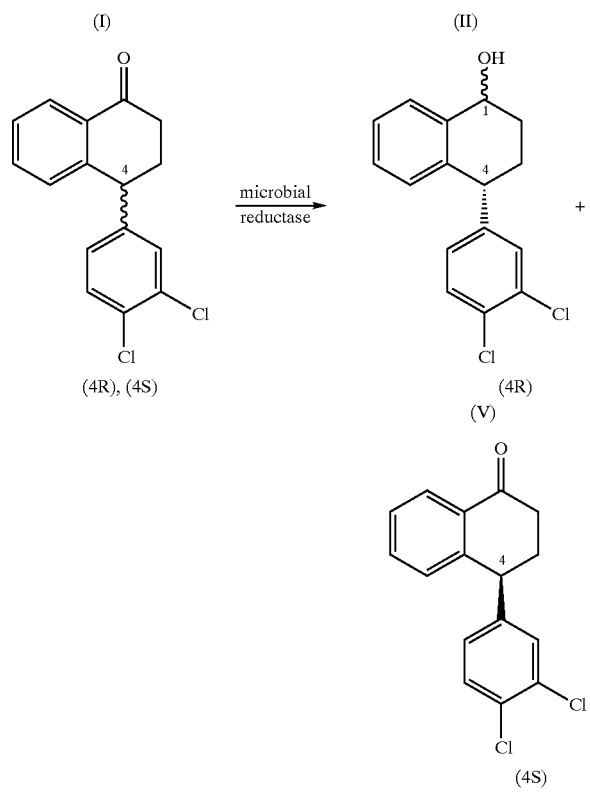

which comprises: contacting a compound of formula (I) with a microorganism, or an enzyme reduction system capable of accomplishing the subject reduction comprising an enzyme derived from said microorganism and a co-factor for said enzyme, and incubating the resulting mixture under conditions sufficient to yield the (4R) tetralol of formula (II) and to leave substantially unreacted the (4S) tetralone of formula (V) or "chiral tetralone." The chiral tetralone can be used in the synthesis of sertraline. The subject process further optionally comprises the separation of the (4S) tetralone of formula (V) from the (4R) tetralol of formula (II). The (4R) tetralol can be recycled to produce the compound of formula (I) and the subject process repeated to result in even more of the desired (4S) tetralone of formula (V).

28 Claims, No Drawings

STEREOSELECTIVE MICROBIAL REDUCTION OF A RACEMIC TETRALONE

CROSSREFERENCE TO RELATED APPLICATION

This application claims priority from U.S. Provisional Patent Application No. 60/106,233 filed Oct. 29, 1998, the benefit of which is hereby claimed under 37 C.F.R. §1.78 (a)(3).

FIELD OF THE INVENTION

The present invention relates to novel processes for preparing the (4S) enantiomer of 4-(3,4-dichlorophenyl)-3,4-dihydro-1(2H)-naphthalenone (hereinafter also referred to as "chiral tetralone" or "(4S) tetralone") and, more specifically, relates to the stereoselective microbial reduction of racemic 4-(3,4-dichlorophenyl)-3,4-dihydro-1(2H)-naphthalenone (hereinafter also referred to as "racemic tetralone") to chiral tetralone.

BACKGROUND OF THE INVENTION

The chiral tetralone prepared by the processes of the present invention may be further reacted to prepare pure cis-(1S)(4S)-N-methyl-4-(3,4-dichlorophenyl)-1,2,3,4-tetrahydro-1-naphthaleneamine, commonly referred to as sertraline. Sertraline is well known to be useful, for example, as an antidepressant and anorectic agent, and in the treatment of chemical dependencies, anxiety-related disorders, premature ejaculation, cancer and post-myocardial infarction.

Methods are known in the art for preparing sertraline, such as, for example, those described in U.S. Pat. Nos. 4,536,518; 4,777,288; 4,839,104; 4,855,500; 4,940,731; 4,962,128; 5,082,970; 5,130,338; 5,196,607; 5,248,699; 5,442,116; 5,463,126; 5,466,880; 5,597,826; and 5,750,794; and, in the paper of W. M. Welch, Jr. et al., appearing in the *Journal of Medicinal Chemistry*, Vol. 27, No. 11, p. 1508 (1984).

Several of the aforementioned patents relate to the synthesis of mixtures of cis- and trans-isomers of racemic N-methyl-4-(3,4-dichlorophenyl)-1,2,3,4-tetrahydro-1-naphthaleneamine. As described therein, the cis- and trans-isomers, as well as their (S) and (R) enantiomers, may be separated by methods known to those skilled in the art including, for example, fractional crystallization or chromatography.

It is also known to select for the ultimately desired chirality earlier on in the synthesis of sertraline. For example, the aforementioned U.S. Pat. No. 5,750,794 discloses a process for preparing chiral tetralone by reacting racemic tetralone with an asymmetric ketone reducing agent to yield the corresponding cis- or trans-alcohols depending upon the chirality of the asymmetric reagent employed, and then separating the alcohols and oxidizing the (1S,4S) and/or (1R,4S) alcohols to (4S)-tetralone.

It is also known in the art that chiral compounds can be synthesized using microorganisms, such as, fungi, e.g., yeast. For example, the use of yeasts to reduce ketones to chiral alcohols is well known. However, as is appreciated by those of skill in the relevant art, the chemical and optical yields, e.g., particular enantiomers and amounts thereof, of such microbial reductions generally vary substantially depending on, for example, the particular microorganism chosen, as well as the substituents of the starting material.

U.S. Pat. No. 5,049,497 discloses a process for resolving a racemic derivative of bicyclo[4.2.0]octane by contacting the derivative with Baker's Yeast under conditions sufficient to give a mixture of a ketone and an alcohol of high enantiomeric purity. As described therein, only one enantiomer of the subject racemic ketone is reduced to give an alcohol.

U.S. Pat. No. 5,580,764 discloses an asymmetric reduction process which uses an intact microorganism, or a broken cell preparation thereof, to convert a cyclic ketone to the corresponding chiral alcohol.

U.S. Pat. No. 5,618,707 discloses a process for the stereoselective reduction of ketone substrates by adding the substrates to a culture broth of either *Zygosaccharomyces bailii* ATCC (American Type Culture Collection) No. 38924 or *Schizosaccharomyces octosporus* ATCC No. 2479, incubating the resultant mixture, and isolating the hydroxy compound through conventional means such as, for example, extraction with organic solvents, adsorption to resins, or chromatography for subsequent use as an intermediate in the preparation of a serum cholesterol lowering agent. The isolated hydroxy compound described therein was analyzed by chiral high performance liquid chromatography (HPLC), reverse-phase HPLC, or both. Consistent with what would be understood by one of skill in the relevant art, as described therein, many of the large number of microorganisms which were investigated for their ability to reduce the ketone group of the selected substrate failed to reduce the ketone group with the desired specificity or productivity.

It has now been unexpectedly found that a range of microorganisms, including fungi, e.g., yeasts, and actinomycetes, substantially stereoselectively reduce a racemic tetralone. More specifically, the subject stereoselective microbial reduction selectively reduces the (4R) tetralone of the racemic mixture while leaving the (4S) tetralone substantially unreacted. Moreover, the unwanted (4R) tetralol produced by the subject process can be oxidized and then racemized to racemic tetralone and the subject process repeated to yield even more (4S) tetralone. The (4S) tetralone produced by the subject process can be used in the synthesis of sertraline.

All of the documents cited herein, including the foregoing, are incorporated by reference herein in their entireties.

SUMMARY OF THE INVENTION

The present invention relates to microbiological reduction of carbonyl groups which comprises contacting a ketone compound, the racemic tetralone of formula (I), with a microorganism, or an enzyme reduction system capable of accomplishing the subject reduction comprising an enzyme derived from said microorganism and a co-factor for said enzyme, and incubating the resultant mixture under suitable conditions such that a compound having a hydroxy group, specifically, the (4R) tetralol of formula (II) can be formed and accumulated in the medium, and a compound having the desired stereochemistry, the (4S) tetralone of formula (V) below, remains substantially unreacted. The (4S) tetralone of formula (V) below, i.e., chiral tetralone, can then be isolated by any suitable method, e.g., chromatography or crystallization. In addition, the (4R) tetralol of formula (II) can be separated from the compounds of formulae (III)–(V), oxidized and racemized to racemic tetralone and the subject stereoselective microbial reduction repeated to result in even more of the desired chiral ketone.

Accordingly, the present invention provides processes for carrying out the following stereospecific microbial reduction:

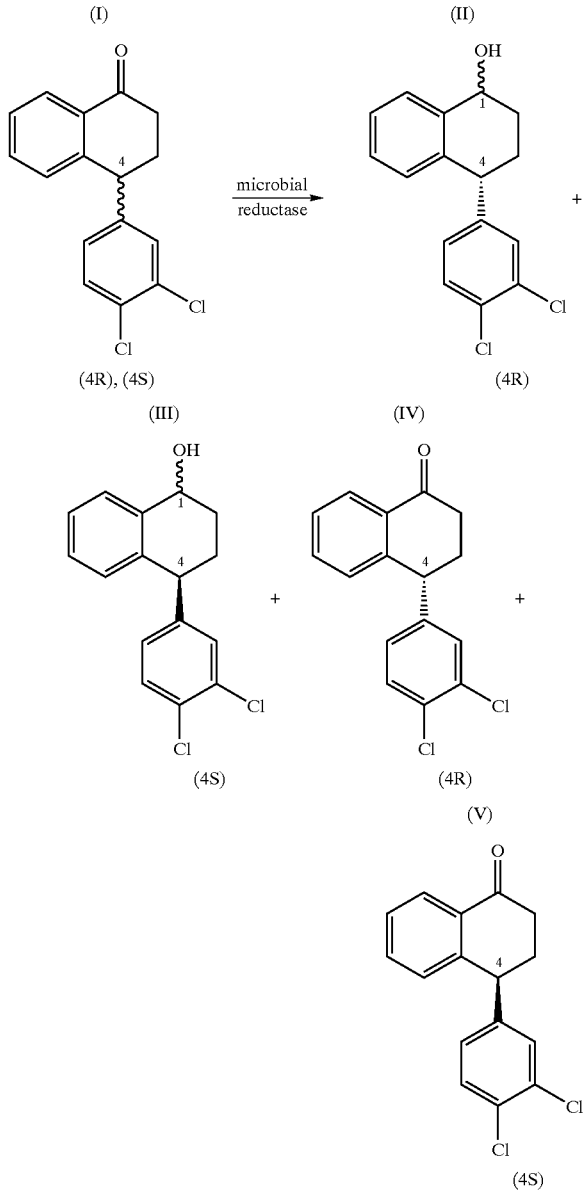

which comprises: contacting a compound of formula (I) with a microorganism, or an enzyme reduction system capable of accomplishing the subject reduction comprising an enzyme derived from said microorganism and a co-factor for said enzyme, and incubating the resulting mixture under conditions sufficient to yield more of the compound of formula (II) than the compound of formula (III), thus leaving more of the compound of formula (V) unreacted than the compound of formula (IV) unreacted.

The subject stereospecific reduction may also be represented by:

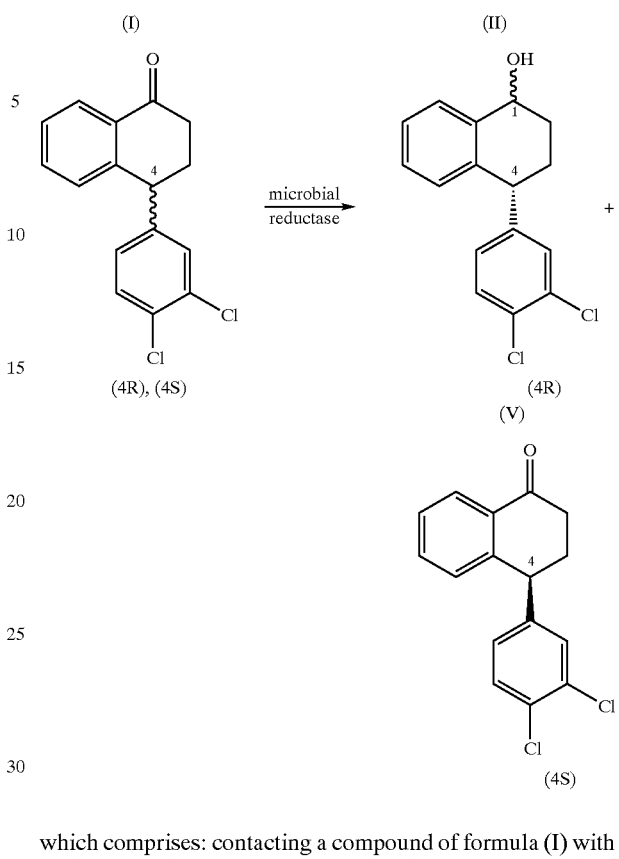

which comprises: contacting a compound of formula (I) with a microorganism, or an enzyme reduction system capable of accomplishing the subject reduction comprising an enzyme derived from said microorganism and a co-factor for said enzyme, and incubating the resulting mixture under conditions sufficient to yield the (4R) tetralol of formula (II) and to leave substantially unreacted the (4S) tetralone of formula (V).

The stereoselective reduction further optionally comprises the separation of the (4S) tetralone of formula (V) from the (4R) tetralol of formula (II). The (4R) tetralol may then be oxidized to produce the (4R) tetralone, which is then reacted, e.g., with a base, to produce racemic tetralone of formula (I) and the subject stereoselective microbial reduction may be repeated to result in even more of the desired (4S) tetralone of formula (V), i.e., the (4S) enantiomer of the racemic tetralone of formula (I).

The present invention provides processes which comprise the stereoselective microbial reduction of a compound of formula (I) to a compound of formula (II) by: contacting a compound of formula (I) with a microorganism, or an enzyme reduction system capable of accomplishing the subject reduction comprising an enzyme derived from said microorganism and a co-factor for said enzyme, and incubating the resulting mixture under conditions sufficient to yield a compound of formula (II), whereby substantially more of the compound of formula (V) remains unreacted than the compound of formula (IV) and substantially more of the compound of formula (II) is produced than the compound of formula (III).

In a preferred embodiment the contacting of the compound of formula (I) is with an enzyme reduction system. In another preferred embodiment the contacting of the compound of formula (I) is with an enzyme reduction system wherein the enzyme is immobilized. In a particularly preferred embodiment the contacting of the compound of formula (I) is with an enzyme reduction system derived from *Hansenula polymorpha* ATCC No. 26012.

In another preferred embodiment the microorganism is a broken cell preparation thereof. In yet another preferred embodiment the microorganism is an acetone powder enzymatic preparation thereof.

In an especially preferred embodiment of the present invention an intact microorganism is used. In a preferred embodiment wherein the microorganism is an intact microorganism, the compound of formula (I) is contacted with a fermentation medium, culture broth, or solvent, comprising the microorganism. In another preferred embodiment wherein the microorganism is an intact microorganism, the compound of formula (I) is contacted with washed intact microorganism. In yet another preferred embodiment wherein the microorganism is intact, the compound of formula (I) is contacted with immobilized intact microorganism.

In an especially preferred embodiment of the present invention the microorganism is an intact microorganism which is grown in a fermentation medium and the contacting occurs by the addition of the compound of formula (I) thereto.

In another especially preferred embodiment of the present invention the microorganism is an intact microorganism which is grown in a growth medium for about forty-eight hours, and the contacting occurs in such growth medium by the addition of the compound of formula (I) thereto, and the incubation is for about five days.

In another preferred embodiment of the present invention the microorganism is either a fungus, e.g., a yeast, or an actinomycete, or a mutant thereof which is capable of performing the stereoselective reduction.

In yet another preferred embodiment of the present invention the microorganism is a fungus. In still another preferred embodiment wherein the microorganism is a fungus, the fungus is *Absidia coerulea* ATCC No. 20137.

In a particularly preferred embodiment of the present invention the microorganism is a yeast. In an especially preferred embodiment of the present invention wherein the microorganism is a yeast, the yeast is *Hansenula polymorpha* ATCC No. 26012, also deposited as ATCC No. 74449.

Where *Hansenula polymorpha* ATCC No. 26012, also deposited as ATCC No. 74449, is employed as the microorganism, the subject stereoselective microbial reduction appreciably reduces only one enantiomer of the compound of formula (I), to give the corresponding alcohol, i.e., the compound of formula (II), while leaving the other enantiomer of the compound of formula (I), i.e., the compound of formula (V), substantially unreacted.

As discussed earlier, the processes of the present invention further optionally include the separation, e.g., carried out using crystallization or chromatography, of the compound of formula (V) from the compounds of formulae (II)–(IV), and the use of such separated compound of formula (V) in the synthesis of sertraline using any known methods therefor.

As also discussed earlier, it is preferred to oxidize the isolated (4R) tetralol of formula (II) to the (4R) tetralone of formula (IV). It is then further preferred to racemize, preferably by reacting the (4R) tetralone with a base, the (4R) tetralone of formula (IV) to the racemic tetralone of formula (I). The oxidation and racemization recycles the unwanted (4R) tetralol for another round of stereoselective microbial reduction according to the processes of the present invention. The recycling of the unwanted (4R) tetralol increases the amount of the desired (4S) tetralone and decreases the amount of unwanted (4R) tetralol discarded. The oxidation and the racemization of the oxidized product may be carried out using any suitable known methods therefor.

DETAILED DESCRIPTION OF THE INVENTION

Those skilled in the art will fully understand the terms used herein to describe the present invention; nonetheless, the following terms used herein, are as described immediately below.

"Co-factor" means any suitable co-factor comprising the enzyme reduction system such as, for example, NADH, NADPH, FADH, FMNH, and/or PQQ or any suitable co-factor which occurs with the enzyme in the microorganism. "Enzyme reduction system" means a suitable microbial oxidoreductase enzyme and the reduced form of a co-factor for the oxidoreductase enzyme, where the co-factor may either be derived from the selected microorganism or may be from any suitable source. The enzyme comprising the enzyme reduction system may be in either free or immobilized form, e.g., in a column or attached to a bead.

"Microbial reduction" means the stereoselective reduction of the present invention as accomplished by the enzyme reduction system, the microbial reductase comprising the enzyme reduction system, the intact microorganism, or any preparation thereof, and the like.

"Microorganism" includes any intact microorganism or preparation therefrom, including, for example, a broken cell preparation of the microorganism; a dehydrated preparation of the microorganism, e.g., an acetone powder enzymatic preparation; microorganism washed free of, e.g., fermentation medium, culture broth, and the like; microorganism immobilized, e.g., in a column, attached to beads, and the like.

The processes provided by the present invention comprise the stereoselective microbial reduction of a compound of the formula (I) to a compound of the formula (II):

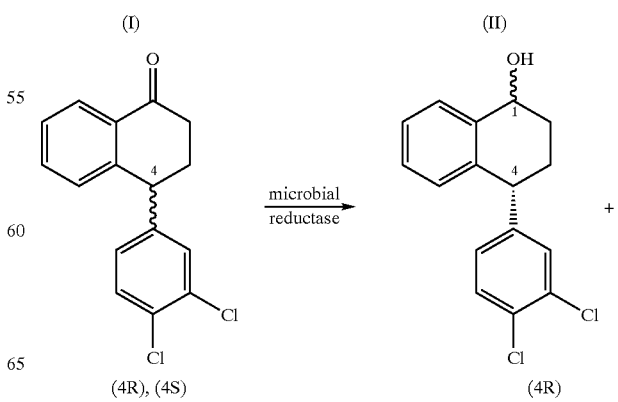

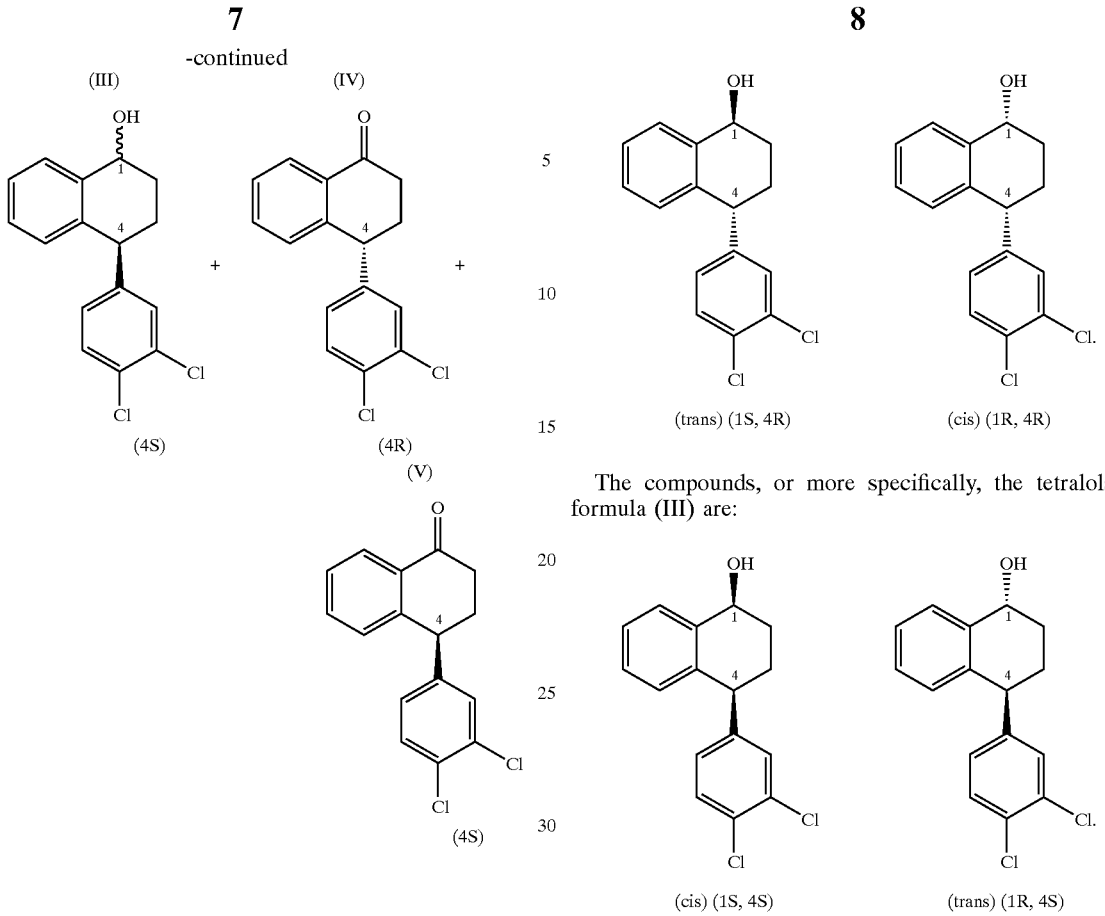

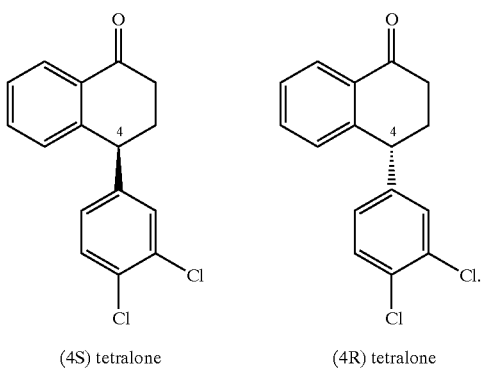

by contacting a compound of formula (I) with a microorganism, or an enzyme reduction system capable of accomplishing the subject reduction comprising an enzyme derived from said microorganism and a co-factor for said enzyme, and incubating the resulting mixture under conditions sufficient to yield a compound of formula (II), whereby substantially more of the compound of formula (V) remains unreduced than the compound of formula (IV) and substantially more of the compound of formula (II) is produced than the compound of formula (III).

As would be understood by those skilled in the art, the compound of formula (I), racemic tetralone, is a mixture of (4S) tetralone and (4R) tetralone as shown below:

The compounds, or more specifically, the tetralols of formula (II) are:

The compounds, or more specifically, the tetralols of formula (III) are:

The compounds of formulae (II) and (III) are disclosed and claimed in the aforementioned U.S. Pat. No. 5,750,794.

The desired compound of formula (V) may be isolated as described below from the undesired compounds of formula (II), and any of the compounds of formulas (III) or (IV) which may have been either produced or remained unreacted, respectively, depending upon, e.g., the microorganism selected and the conditions of incubation.

The compounds of formula (II) may be converted to a compound of formula (I), e.g., by oxidization and racemization, and run through the subject stereoselective microbial reduction to result in yet another amount of the (4S) tetralone of formula (V).

The process of the present invention is readily carried out. Thus, the microorganism is either fermented (intact microorganism) or incubated (broken cell preparation, dehydrated preparation, or any other suitable preparation of the microorganism) in the presence of the racemic tetralone, represented by formula (I), to modify racemic tetralone, and more particularly, to reduce the undesired (4R) enantiomer of the racemic ketone to its corresponding alcohol, represented by formula (II), while leaving the desired (4S) enantiomer, represented by formula (V), substantially unreacted, thereby, in one step, resulting in the optically enriched (4S) enantiomer. The (4S) enantiomer may then be further reacted by methods well known to those skilled in the relevant art such as described, for example, in the aforementioned U.S. Pat. Nos. 4,536,518; 4,777,288; 4,839,104; 4,855,500; 4,940,731; 4,962,128; 5,082,970; 5,130,338; 5,196,607; 5,248,699; 5,442,116; 5,463,126; 5,466,880; 5,597,826; and 5,750,794; and, in the aforementioned paper of W. M. Welch, Jr. et al., to ultimately yield sertraline.

The activity, methods for testing activities, dosages, dosage forms, methods of administration and background information concerning sertraline are set forth, for example, in the aforementioned U.S. Pat. Nos. 4,536,518; 4,777,288; and 4,839,104; and the aforementioned paper by W. M. Welch, Jr. et al.

Any suitable microorganism may be used in the process of the present invention. As described earlier, the microorganism used in the subject process may be intact, any suitable preparation thereof, e.g., a broken cell preparation thereof, a dehydrated preparation thereof, and be either free or immobilized. However, where a non-intact microorganism is employed in the present invention such as, for example, a broken cell preparation, e.g., cell extract, acetone powder enzymatic preparation, or the enzyme derived therefrom, those skilled in the art would understand that a suitable co-factor for the enzyme is also included.

Those skilled in the art will understand from the description provided herein and their related knowledge how to prepare a suitable broken cell preparation such as described, for example, by R. N. Patel et al. in the article "Oxidation of Secondary Alcohols to Methyl Ketones by Yeasts" published in *Applied and Environmental Microbiology,* 38(2): 219–223 (1979).

Those skilled in the art will understand from the description provided herein and their related knowledge how to prepare a suitable acetone powder enzymatic preparation such as described, for example, by K. Nakamura et al. in the article "Asymmetric Reduction of Ketones by the Acetone Powder of *Geotrichum candidum*" published in *Tetrahedron Letters,* 37(10): 1629–1632 (1996).

In addition, an enzyme (e.g., an oxidoreductase) of any suitable microorganism may also be used in the subject processes, and this enzyme may be isolated from the microorganism by any suitable method known to those skilled in the art and, as for the intact microorganism, may be used in the subject process in either free or immobilized form. Those skilled in the art will understand from the description provided herein and their related knowledge how to isolate and purify the enzyme of the suitable microorganism such as generally described, for example, in the articles by: M. Wada et al., "Purification and Characterization of NADPH-Dependent Carbonyl Reductase, Involved in Stereoselective Reduction of Ethyl 4-Chloro-3-oxobutanoate, from *Candida magnoliae*" published in *Biosci. Biotechnol. Biochem,* 62(2): 280–285 (1998), P. Trost et al., "Purification and Properties of NAP(P)H:(quinone-acceptor) oxidoreductase of sugarbeet cells" published in *Eur. J. Biochem.,* 234: 452–458 (1995), K. M. Madyastha and T. L. Gururaja, "Purification and Some of the Properties of a Novel Secondary Alcohol Dehydrogenase from *Alcaligenes eutrophus*" published in *Biochemical and Biophysical Research Communications,* 211(2): 540–546 (1995), O. Bortolini et al., "Kinetic resolution of vic-diols by *Bacillus stearothermophilus* diacetyl reductase" published in *Tetrahedron: Asymmetry,* 9: 647–651 (1998), R. N. Patel et al., "Stereospecific microbial reduction of 4,5-dihydro-4-(4-methoxyphenyl)-6-(triflurormethyl-1H-1)-benzazepin-2-one" published in *Enzyme Microb. Technol.,* 3: 906–912 (1991) and R. N. Patel et al., "Stereoselective microbial/enzymatic oxidation of (exo, exo)-7-oxabicyclo [2.2.1] heptane-2,3-dimethanol to the corresponding chiral lactol and lactone" published in *Enzyme Microb. Technol.,* 14: 778–784 (1992); and by U.S. Pat. No. 5,523,223 and the aforementioned U.S. Pat. No. 5,580,764.

Suitable microorganisms include *Hansenula polymorpha* ATCC No. 26012, *Hansenula polymorpha* ATCC No. 74449, *Absidia coerulea* ATCC No. 20137, *Geotrichum candidum* ATCC No. 34614, *Geotrichum candidum* ATCC No. 62401, *Mortierella isabellina* ATCC No. 42613, *Mortierella isabellina* ATCC No. 38063, *Mortierella vinacea* ATCC No. 09515, *Penicillium notatum* ATCC No. 36740, *Blastoschizomyces capitatus* ATCC No. 28575, *Monosporium olivaceum* v. *major* ATCC No. 36300, *Aureobasidium pullulans* ATCC No. 16623, *Debaryomyces polymorphus* ATCC No. 20280, *Saccharomyces cerevisiae* ATCC No. 15248, *Candida schatavii* ATCC No. 24409, *Pichia fabianii* ATCC 16755 and *Streptomyces rimosus* ss. *rimosus* ATCC No. 10970; and mutants thereof which are known or otherwise obtainable by those skilled in the relevant art and able, despite such mutation, to accomplish the stereoselective microbial reduction disclosed herein.

Preferred intact microorganisms will be those which substantially reduce the (4R) tetralone while leaving the (4S) tetralone substantially unreacted where reacted includes reduction or any other intrinsic activity which might degrade or otherwise negatively impact the desired (4S) tetralone at any stage of the subject process. As would be appreciated by those skilled in the art from the disclosure herein, such unwanted reaction of the (4S) tetralone may be substantially prevented by, for example, using the enzyme derived from the selected microorganism versus the intact microorganism.

The microorganisms suitable for use in the subject stereospecific microbial reduction may be prepared by any suitable method known to those skilled in the relevant art. An example of a suitable method for the preparation of a microorganism from a commercially purchased stock is provided below. The method provided below may be used for any microorganism suitable for use in the present inventive process, and those skilled in the art would understand from the description provided herein how to modify any part of the procedure, e.g., method of preparing the microorganism, intact or preparation, e.g., broken cell or dehydrated, thereof, free or immobilized; method of preparing a suitable enzyme derived from such microorganisms; method of contacting of the racemic tetralone with the microorganism or the enzyme comprising the enzyme reduction system derived therefrom; growth medium components and conditions, e.g., temperature, pH and the like; or incubation conditions; to achieve the desired result in any particular process.

Those skilled in the art will understand from the description provided herein and their related knowledge how to prepare suitable immobilized intact microorganism such as described, for example, by A. Bauer et al. in the article "Polyvinyl alcohol-immobilized whole-cell preparations for biotransformation of nitrites" published in *Biotechnology Letters,* 18(3): 343–348 (March 1996).

Any suitable method of contacting the compound of formula (I) with the microorganism or enzyme reduction system may be used in the present invention. The compound of formula (I) may be contacted with the microorganism or the enzyme reduction system in any suitable order. For example, the compound of formula (I) may be added to a medium, such as a culture broth, comprising the microorganism, free or immobilized, or some combination thereof; or the medium may comprise the compound of formula (I) and the microorganism may then be added to such medium; or the compound of formula (I) and the microorganism may be added together to such medium; or the compound of formula (I) may be added to a broken cell preparation thereof; or the compound of formula (I) may be added to a dehydrated preparation of the microorganism; or either the compound of formula (I) or the microorganism or enzyme reduction system may be added to a suitable solvent comprising the other; and the like. Those skilled in the art will understand from the description provided herein how to modify any part of the subject process as so desired.

It is especially preferred in the present invention that the microorganism, or the enzyme reduction system, is derived from *Hansenula polymorpha* ATCC No. 26012. A lyophilized sample of *Hansenula polymorpha* ATCC No. 26012 (originally contributed by D. W. Levine) was deposited with the ATCC located at 10801 University Boulevard, Manassas, Va., 20110–2209, U.S.A., under the terms of the Budapest Treaty on Jun. 26, 1998. This newly deposited culture was given the new deposit number of ATCC No. 74449. Hence, it is also especially preferred in the present invention that the microorganism is *Hansenula polymorpha* ATCC No. 74449. All restrictions on the availability to the public of the microorganism culture so deposited will be irrevocably removed upon the issuance of a patent from the specification of the present invention.

Cultures of *Hansenula polymorpha* ATCC No. 26012 can be obtained from the ATCC, and an example of a suitable method for its preparation from such a commercially purchased stock is provided immediately below. A culture so obtained is added to a suitable growth medium, and is incubated with shaking until growth occurs, both steps as would be appreciated by those skilled in the art. The culture, thus prepared, can be used to inoculate slants, with portions of these slants frozen as master stocks. Alternatively, liquid stock cultures can be prepared to which glycerol is added to from about 10% to about 20% which are then frozen at about −80° C., preferably in small cryotubes.

As would be understood by those skilled in the art for any microorganism selected, and as provided specifically hereinafter in the examples for *Absidia coerulea* ATCC No. 20137 and the especially preferred *Hansenula polymorpha* ATCC No. 26012 or ATCC No. 74449, a suitable method for preparing the microorganism is as follows: the microorganism is inoculated from a frozen stock culture such as described above (about a 17% glycerol stock) into a flask or a glass tube with a metal closure containing a growth medium (containing an aliquot from a sterile solution which includes Tween® 80, glycerol and distilled water) whose composition is described in more detail below. The fermentation is carried out at temperatures ranging from about 22° C. to about 32° C., and preferably at about 29° C., with suitable shaking, preferably from about 200 rpm to about 220 rpm, and most preferably, at about 210 rpm. Where so desired, the pH of the growth medium can be maintained by the use of suitable buffers incorporated into the fermentation medium and/or periodically adjusted by addition of either base or acid as so required.

Any suitable duration of growth of the microorganism, contacting of the microorganism with the compound of formula (I), and incubation of the compound of formula (I) with the microorganism may be used in the present invention. Suitable growth of the microorganism may be achieved, e.g., within about 24 hours, at which time a suitable aliquot of a solution of racemic tetralone in a suitable solvent, preferably ethanol, may be added to the culture. The fermentation may then be continued for, e.g., from about two to about six days, and preferably, e.g., for about five days, at which time the fermentation broth may be extracted using any suitable extraction method whereby a suitable solvent, such as, for example, ethyl acetate, methyl isobutylketone, methyl ethylketone, methylene chloride, and the like, preferably, ethyl acetate, removes the organic components from the fermentation broth. After extraction of the fermentation broth and separation of the organic and aqueous phases, the compounds comprising the organic residue may be determined using any suitable method, such as, for example, chromatography, preferably, chiral HPLC.

Any suitable growth medium may be used in the process of the present invention, and the suitable growth medium will contain a source or sources of assimilable carbon, assimilable nitrogen and inorganic salts containing essential minerals. In general, many carbohydrates such as, for example, glucose, maltose, mannose, sucrose, starch, glycerin, millet jelly, molasses, soy bean, and the like, can be used as sources of assimilable carbon. Sources of assimilable nitrogen include, for example, materials such as yeast and casein hydrolysates, primary yeast, yeast extracts, cottonseed flour, soybean solids, wheat germ, meat extracts, peptone, corn steep liquor, and ammonium salts. Suitable inorganic salt nutrients for use in the culture medium of the present invention include, for example, the customary salts containing sodium, iron, magnesium, potassium, cobalt, phosphate, and the like. More particularly, growth media suitable for use in the present invention include, for example:

(a) dextrose (about 20 gram (g)), yeast extract (about 5 g), soy flour (about 5 g), NaCl (about 5 g), $K_2HPO_4$ (about 5 g), and distilled $H_2O$ (about 1 liter (L)), pH adjusted to about pH 7.0 with $H_2SO_{4(aq.)}$;

(b) dextrin (about 10 g), beef extract (about 3 g), ardamine pH (about 5 g), NZ amine type E (about 5 g), $MgSO_4 7H_2O$ (about 0.5 g), $KH_2PO_4$ (about 0.37 g), $CaCO_3$ (about 0.5 g), and distilled $H_2O$ (about 1 L), pH adjusted to about pH 7.1 with $HCl_{(aq.)}$, followed by a second stage of glucose (about 10 g), Hy-Case SF® (about 2 g), beef extract (about 1 g), corn steep liquor (about 3 g), and distilled $H_2O$ (about 1 L), pH adjusted to about pH 7.0;

(c) glucose (about 10 g), corn steep liquor (about 6 g), $KH_2PO_4$ (about 3 g), $CaCO_3$ (about 3.5 g), soybean oil (crude, about 2.2 milliliters (ml)), yeast extract (about 2.5 g), and distilled $H_2O$ (about 1 L), pH adjusted to from about pH 7.0 to about pH 7.3 with $HCl_{(aq.)}$;

(d) malt syrup (about 20 g), soybean meal (about 5 g), casein (about 1 g), dried yeast (about 1 g), NaCl (about 5 g), and distilled $H_2O$ (about 1 L);

(e) lactose (about 75 g), Pharmamediae® (substitute yeast extract, about 40 g), $CaCO_3$ (about 10 g), $Na_2SO_4$ (about 4 g), and distilled $H_2O$ (about 1 L);

(f) ISP #2 (see, e.g., page 460 of the *Handbook of Microbial Media* by R. M. Atlas, edited by L. C. Parks, CRC Press, Inc., 1993, ("Handbook"));

(g) ISP #3 (see, page 460 of the *Handbook*);

(h) ISP#4 (see, page 461 of the *Handbook*);

(i) ISP#5 (see, pages 461–462 of the *Handbook*); and the like.

A particularly preferred growth medium is 2× of (a) provided above.

Reference to particular buffers, media, reagents, contacting or culture conditions, and the like, is not intended to be limiting, but should be read to include all such related materials that those of ordinary skill in the art would recognize as being of interest or value in the particular context in which the discussion herein is presented. For example, it is often possible to substitute one buffer system or culture medium for another, such that a different but known way is used to achieve the same goals as those to which the use of a suggested method, material or composition is directed. Moreover, it should be understood that the present invention includes the scaling-up of the subject process for commercial purposes.

Hence, as would be understood by those of ordinary skill in the art, variation of the growth medium, the conditions of fermentation, and/or the amount of racemic tetralone may be altered to control the yield of the resultant compounds and their relative rates of production. In general, the techniques employed in the present invention will be chosen with regard to industrial efficiency. The growth media, conditions of fermentation and relative amounts of microorganism, or enzyme reduction system, and racemic tetralone described herein are merely illustrative of the wide variety of media, fermentation conditions and amounts of starting materials which may be suitably employed in the present invention as would be appreciated by those skilled in the art, and are not intended to be limiting in any way.

Any suitable methods for isolating and/or purifying any of the products of the subject process may be used in the present invention including filtration, extraction, crystallization, column chromatography, thin-layer chromatography, preparative low pressure liquid chromatography or HPLC, or any suitable combination of such methods.

Further, one of skill in the art would appreciate that the unwanted corresponding alcohol of the (4R) tetralone, the compound of formula (II), produced by the processes disclosed herein, may be recycled, e.g., oxidized and racemized as discussed earlier herein, by any suitable known method to a racemic tetralone of formula (I), and the processes of the present invention repeated to result in, once again, the desired (4S) tetralone of formula (V). The oxidation of the (4R) tetralol to the (4R) ketone can be done by methods known to those skilled in the art. The racemization reaction may be performed in any suitable manner but is generally performed at a temperature of from about 0° C. to about 100° C., preferably from about 25° C. to about 65° C. The (4R) tetralone is reacted with a base at a temperature of from about 25° C. to about 85° C., preferably from about 50° C. to about 65° C. Suitable bases for this racemization reaction include potassium t-butoxide, sodium hydroxide, sodium methoxide and potassium hydroxide. A preferred base is potassium t-butoxide.

The detailed examples provided below show that a range of microorganisms, including fungi, e.g., yeasts, and actinomycetes, stereoselectively reduce racemic tetralone, to yield the desired (4S) tetralone of formula (V), i.e., chiral tetralone, which may then be separated from the unwanted compounds and further reacted according to methods well known in the art to yield sertraline.

The present invention is illustrated by the following examples. The foregoing and following description of the present invention and the various embodiments are not intended to be limiting of the invention but rather are illustrative thereof. Hence, it will be understood that the invention is not limited to the specific details of these examples.

EXAMPLE I

Reduction of a Racemic Tetralone

Using *Hansenula polymorpha* ATCC No. 26012
A. Fermentation of the Yeast *Hansenula polymorpha* ATCC No. 26012

One "control" culture (C1) and one "test" culture (T1) were prepared as follows: about 2.5 ml of sterile growth medium (about 40 g/l of dextrose, about 10 g/l of nutrisoy flour, about 10 g/l of yeast extract, about 10 g/l of NaCl and about 10 g/l of $K_2HPO_4$, with the pH adjusted to about 7.0 with $H_2SO_4$) was added to each of two 16×125 mm glass tubes each having a metal closure (C1, T1), followed by the addition of about 0.2 ml of a solution A (about 25 g of Tween® 80, about 100 g of glycerol and about 250 ml of distilled water, filter-sterilized) to each of the two cultures.

About 25 $\mu$l of about a 17% frozen glycerol stock of *Hansenula polymorpha* ATCC No. 26012 was inoculated into T1. The two tube cultures were incubated at about 29° C., with shaking at about 210 rpm. After about 24 hours, about 50 $\mu$l of a stock solution (about 5 mg/ml in about 100% ethanol, final concentration of about 100 $\mu$g/ml) of a racemic tetralone (compound of formula (I) comprising the compounds of formulae (IV) and (V), at about 5 mg/ml in ethanol) was added to C1 and T1.

After about five days, one ml of NaCl (sat'd.) was added to each of the two tube cultures. The fermentation broth of each tube culture (about 3.6 ml) was extracted with an equal volume of ethyl acetate (neat): the ethyl acetate was added, the tube culture was vortexed and then centrifuged at about 2,000 rpm (IEC® Centrifuge, 300 Second Avenue, Needham Heights, Mass. 02194). The ethyl acetate layer was removed and the aqueous layer extracted for a second time. The combined organic extracts were dried down, under nitrogen, in a water bath at about 50° C.

B. Configuration of the Residual Ketone: Compounds of Formulae (IV) and (V)

Each of the extracts, prepared as described above, was resuspended in about one ml of ethanol, and about 20 $\mu$l of each resuspended extract was analyzed by injection onto an HPLC column: Chiralcel OK guard column (4.6×50 mm, Diacel Chemical Industries, LTD., 730 Springdale Drive, P.O. Box 564, Exton, Pa. 19341) coupled to a Chiralcel OK column (4.6×250 mm, Daicel). The compounds contained within each injected resuspended extract were separated isocratically at about 0.8 ml per minute in a mobile phase (ethanol:ethyl acetate, 85:15), and the compounds comprising the extracts were detected using a 996 PDA detector (Waters®, 34 Maple Street, Milford, Mass. 01757) set at 254 nm.

As illustrated by the data for C1 and T1 of TABLE I below, chiral HPLC analysis shows that the inclusion of the microorganism, i.e., *Hansenula polymorpha* ATCC No. 26012, results in a ratio of 16:1 ((4S) tetralone of formula (V) unreacted: versus (4R) tetralone of formula (IV) unreacted), which further illustrates the stereospecificity of the subject microbial reduction process. The results reported below are based on the known amount of each enantiomer added (about 50 $\mu$g/ml each of the compounds of formulae (IV) and (V)). As mentioned above, the starting racemic tetralone of formula (I) had a concentration of about 100 $\mu$g/ml.

TABLE I

| CULTURE | 4S TETRALONE ($\mu$g/ml) | 4R TETRALONE ($\mu$g/ml) | 4S:4R |
|---------|--------------------------|--------------------------|-------|
| C1      | 42.63                    | 43.04                    | 1     |
| T1      | 37.92                    | 2.37                     | 16    |

The results from the chiral analysis show that the *Hansenula polymorpha* ATCC No. 26012 culture (T1) substantially reduces the (4R) tetralone while leaving substantially unreacted the (4S) tetralone (about 4.7% (4R) tetralone remains versus about 76% of the (4S) tetralone). The (4S) tetralone was determined to be present in about 88% ee ("percent amount of enantiomeric excess") by such chiral HPLC. As also shown by the data of TABLE I, specifically by the ratio of (4S):(4R), i.e., 16, substantially more (4S) tetralone remains unreacted than (4R) tetralone.

Accordingly, the inclusion of the intact microorganism, i.e., *Hansenula polymorpha* ATCC No. 26012, resulted in the stereospecific reduction of substantially more of the starting (4R) tetralone of formula (IV) than the starting (4S) tetralone of formula (V) ((4S):(4R)), and yielded mostly the (4R) tetralol of formula (II) versus the (4S) tetralol of formula (III) (data not shown). The majority of the (4R) tetralol yielded was the (1S,4R) tetralol, and the majority of the minor amount of (4S) tetralol yielded was the (1S,4S) tetralol.

EXAMPLE II

Reduction of a Racemic Tetralone

Using *Absidia coerulea* ATCC No. 20137

A. Fermentation of the Fungus *Absidia coerulea* ATCC No. 20137

One "control" culture (C2) and one "test" culture (T2) were prepared as follows: about 2.5 ml of sterile growth medium (about 20 g/l of dextrose, about 5 g/l of nutrisoy flour, about 5 g/l of yeast extract, about 5 g/l of NaCl and about 5 g/l of $K_2HPO_4$, with the pH adjusted to about 7.0 with $H_2SO_4$) was added to each of two 16×125 mm glass tubes each having a metal closure (C2, T2).

About 25 µl of about a 17% frozen glycerol stock of *Absidia coerulea* ATCC No. 20137 was inoculated into T2. The two tube cultures were incubated at about 29° C., with shaking at about 210 rpm. After about 48 hours, about 50 µl (about 5 mg/ml in ethanol, final concentration of about 100 µg/ml) of a racemic tetralone (as described in Example I herein, at about 5 mg/ml in about 100% ethanol) was added to C2 and T2.

After about five days, one ml of NaCl (sat'd.) was added to each of the two tube cultures. The fermentation broth of each tube culture (about 3.6 ml) was extracted with about 3 ml of ethyl acetate (neat): the ethyl acetate was added, the tube culture was vortexed and then centrifuged at about 2,000 rpm (IEC Centrifuge). The ethyl acetate layer was removed and the aqueous layer extracted for a second time. The combined organic extracts were dried down, under nitrogen, in a water bath at about 50° C.

B. Configuration of the Residual Ketone: Compounds of Formulae (IV) and (V)

Each of the extracts, prepared as described above, was resuspended in about one ml of ethanol, and about 20 µl of each resuspended extract was analyzed by injection onto an HPLC column: Chiralcel OK guard column (4.6×50 mm) coupled to a Chiralcel OK column (4.6×250 mm). The compounds contained within each injected resuspended extract were separated isocratically at about 0.8 ml per minute in a mobile phase (ethanol:ethyl acetate, 85:15), and the compounds comprising the extracts were detected using a 996 PDA detector (Waters® set at 254 nm.

As illustrated by the HPLC data for C2 and T2 shown below, the inclusion of the microorganism, i.e., *Absidia coerulea* ATCC No. 20137, resulted in the stereospecific reduction of more of the starting (4R) tetralone of formula (IV) than of the starting (4S) tetralone of formula (V).

More specifically, the results from the chiral analysis show that the *Absidia coerulea* ATCC No. 20137 culture reduces the (4R) tetralone while leaving substantially unreacted the (4S) tetralone (about 13.6% (4R) tetralone remains versus about 40.5% of the (4S) tetralone. The (4S) tetralone was determined to be present in about 50% ee by such chiral HPLC.

As illustrated by the data for C2 and T2 of TABLE II below, chiral HPLC analysis shows that the inclusion of the microorganism, i.e., *Absidia coerulea* ATCC No. 20137 (T2), results in a ratio of at least twice as much of the (4S) tetralone left unreduced versus unreduced (4R) tetralone, further evidencing the stereospecificity of the subject microbial reduction process. The results reported below are based on the known amount of each enantiomer added (about 50 µg/ml each as described in Example I herein). As mentioned above, the starting racemic tetralone had a concentration of about 100 µg/ml.

TABLE II

| CULTURE | 4S TETRALONE (µg/ml) | 4R TETRALONE (µg/ml) | 4S:4R |
|---|---|---|---|
| C2 | 39.53 | 39.47 | 1 |
| T2 | 20.24 | 6.81 | 3 |

EXAMPLE III

Reduction of a Racemic Tetralone

Using Fungi, Yeasts and an Actinomycete

As would be understood by those skilled, in the relevant art, for the microorganisms listed in TABLE III which were used in the subject reduction, *Geotrichum candidum* ATCC No. 62401, *Mortierella isabellina* ATCC No. 38063, *Mortierella vinacea* ATCC No. 09515, *Penicillium notatum* ATCC NO. 36740, *Blastoschizomyces capitatus* ATCC No. 28575, *Monosporium olivaceum* v. *major* ATCC No. 36300, *Aureobasidium pullulans* ATCC No. 16623, *Pichia fabianii* ATCC No. 16755 and *Streptomyces rimosus* ss. *rimosus* ATCC NO. 10970 were prepared as described in Example II; *Geotrichum candidum* ATCC No. 34614, *Mortierella isabellina* ATCC No. 42613, *Debaryomyces polymorphus* ATCC NO. 20280 and *Saccharomyces cerevisiae* ATCC NO. 15248 were prepared as described in Example II except that the extraction was repeated; and *Candida schatavii* ATCC No. 24409 was prepared as provided below.

*Candida schatavii* ATCC No. 24409 was prepared and used according to the present invention as follows: about 2.5 ml of sterile growth medium (about 20 g/l of dextrose, about 5 g/l of nutrisoy flour, about 5 g/l of yeast extract, about 5 g/l of NaCl and about 5 g/l of $K_2HPO_4$, with the pH adjusted to about 7.0 with $H_2SO_4$) was added to a 16×125 mm glass tube having a metal closure, followed by the addition of about 0.1 ml of a filter-sterilized solution of about 25 g of Tween® 80, about 100 g of glycerol and about 250 ml of distilled water to the culture. Next, about 25 µl of about a 17% frozen glycerol stock of *Candida schatavii* ATCC No. 24409 was inoculated into the culture. The culture was grown at about 29° C., with shaking at about 210 rpm. After about 48 hours, about 50 µl of a stock solution (about 5 mg/ml in about 100% ethanol, final concentration of about 100 µg/ml) of a racemic tetralone (compound of formula (I) comprising the compounds of formulae (IV) and (V), at about 5 mg/ml in about 100% ethanol) was added to the culture.

After an additional four days, the fermentation broth of the culture (about 2.6 ml) was extracted with an equal volume of ethyl acetate (neat), the culture was vortexed and then centrifuged at about 2,000 rpm (IEC® Centrifuge). The extraction was repeated. The extracts were dried down, under nitrogen, in a water bath at about 50° C. The extract was then resuspended in about one ml of ethanol, and about 5 µl of the resuspended extract was analyzed by injection onto an HPLC column: Chiralcel OD guard column (4.6×50 mm, Diacel Chemical Industries, LTD.) coupled to a Chiralcel OD column (4.6×250 mm, Daicel). The compounds contained within the injected resuspended extract were separated isocratically at about 0.9 ml per minute in a mobile phase (hexane:isopropanol, 95:5), and the compounds comprising the extract were detected using a 996 PDA detector (Waters®) set at 210 nm.

As shown by the chiral HPLC (conducted as in Example I and II) data reported in TABLE III, each of the microorganisms listed in TABLE III below stereospecifically reduced more of the (4R) tetralone than the (4S) tetralone, and resulted generally in a ratio of at least about twice as much of the (4S) tetralone left unreacted versus unreacted (4R) tetralone.

TABLE III

| CULTURE ATCC No., Organism Type | 4S TETRALONE (µg/ml) | 4R TETRALONE (µg/ml) | 4S:4R |
|---|---|---|---|
| *Geotrichum candidum* - 1 34614, Fungus | 18.23 | 7.85 | 2.32 |
| *Geotrichum candidum* - 2 62401, Fungus | 12.16 | 6.17 | 1.97 |
| *Mortierella isabellina* - 1 42613, Fungus | 3.33 | 1.36 | 2.45 |
| *Mortierella isabellina* - 2 38063, Fungus | 2.74 | 0.95 | 2.88 |
| *Mortierella vinacea* 09515, Fungus | 6.01 | 1.45 | 4.14 |
| *Penicillium notatum* 36740, Fungus | 10.39 | 5.50 | 1.89 |
| *Blastoschizomyces capitatus* 28575, Fungus | 9.47 | 4.5 | 2.10 |
| *Monosporium olivaceum* v. major 36300, Fungus | 10.39 | 0.71 | 14.6 |
| *Aureobasidium pullulans* 16623, Fungus | 11.76 | 3.65 | 3.22 |
| *Debaryomyces polymorphus* 20280, Yeast | 7.18 | 3.67 | 1.96 |
| *Saccharomyces cerevisiae* 15248, Yeast | 24.33 | 14.42 | 1.69 |
| *Candida schatavii* 24409, Yeast | 7.18 | 1.03 | 6.97 |
| *Pichia fabianii* 16755, Yeast | 17.89 | 8.97 | 1.99 |
| *Streptomyces rimosus* ss. *rimosus* 16755, Actinomycete | 3.21 | 1.68 | 1.91 |

It should be noted that while intact *Monosporium olivaceum* v. *major* ATCC No. 36300, as illustrated by the data of TABLE III, reduced substantially more of the (4R) tetralone versus the (4S) tetralone, and as such would be a preferred microorganism for use in the subject process, nonetheless, undesirable degradation of both the (4R) tetralone and the (4S) tetralone was also reported for this culture. The undesirable degradation may be due, for example, to other enzymes and the like comprising the intact microorganism. Therefore, as will be understood by those skilled in the art from the description provided herein, it is preferred to use the enzyme isolated from *Monosporium olivaceum* v. *major* ATCC No. 36300 versus intact *Monosporium olivaceum* v. *major* ATCC No. 36300.

What is claimed is:

1. A process for the stereoselective microbial reduction of racemic 4-(3,4-dichlorophenyl)-3,4-dihydro-1(2H)-naphthalenone, where said racemic 4-(3,4-dichlorophenyl)-3,4-dihydro-1(2H)-naphthalenone is a mixture of (4S)-(3,4-dichlorophenyl)-3,4-dihydro-1(2H)-naphthalenone and (4R)-(3,4-dichlorophenyl)-3,4-dihydro-1(2H)-naphthalenone having the formulae

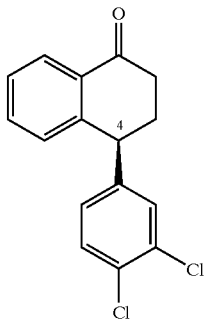

(4S)-(3,4dichlorophenyl)-3,4-dihydro-1(2H)-naphthalenone, and

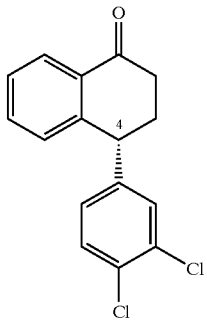

(4R)-(3,4-dichlorophenyl)-3,4-dihydro-1(2H)-naphthalenone,
to a mixture of cis and trans tetralols having the formulae:

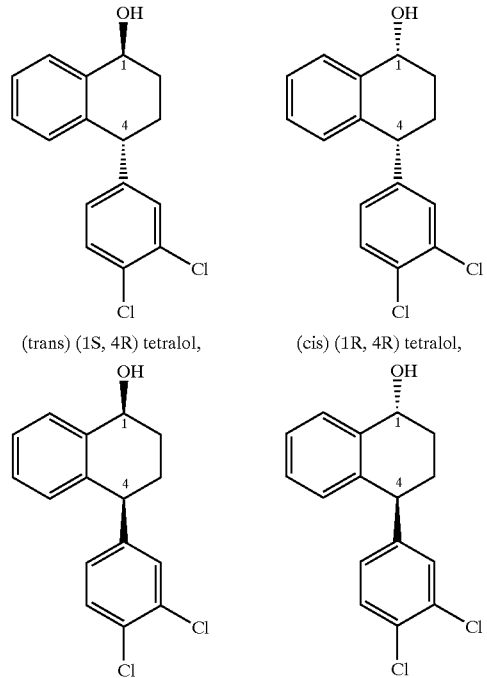

to obtain unreacted (4S)-(3,4-dichlorophenyl)-3,4-dihydro-1(2H)-naphthalenone in an ee of greater than 50%, and unreacted (4R)-(3,4-dichlorophenyl)-3,4-dihydro-1(2H)-naphthalenone in an ee of less than 50%, which comprises:
contacting racemic 4-(3,4-dichlorophenyl)-3,4-dihydro-1(2H)-naphthalenone with a microorganism, or an enzyme reduction system capable of accomplishing said reduction comprising an enzyme obtained from said microorganism and a co-factor for said enzyme;
incubating the resulting mixture under conditions sufficient to yield said (trans) (1S,4R) tetralol, said (cis) (1R,4R) tetralol, said (trans) (1R,4S) tetralol, and said (cis) (1S,4S) tetralol, and to leave substantially unreacted (4S)-(3,4-dichlorophenyl)-3,4-dihydro-1(2H)-naphthalenone, resulting in unreacted (4S)-(3,4-dichlorophenyl)-3,4-dihydro-1(2H)-naphthalenone being present in ee greater than 50%, and unreacted (4R)-(3,4-dichlorophenyl)-3,4-dihydro-1(2H)-naphthalenone being present in ee less than 50%;
wherein said microorganism is selected from the group consisting of *Hansenula polymorpha* ATCC No. 26012, *Hansenula polymorpha* ATCC No. 74449, *Absidia coerulea* ATCC No. 20137, *Geotrichum candidum* ATCC No. 34614, *Geotrichum candidum* ATCC No. 62401, *Mortierella isabellina* ATCC No. 42613, *Mortierella isabellina* ATCC No. 38063, *Mortierella vinacea* ATCC No. 09515, *Penicillium notatum* ATCC No. 36740, *Blastoschizomyces capitalus* ATCC No. 28575, *Monosporium olivaceum* v. *major* ATCC No. 36300, *Aureobasidium pullulans* ATCC No. 16623, *Debaryomyces polymorphus* ATCC No. 20280, *Saccharomyces cerevisiae* ATCC No. 15248, *Candida schatavii* ATCC No. 24409, *Pichi fabianii* ATCC No. 16755 and *Streptomyces rimosus* ss. *rimosus* ATCC No. 10970; and such mutants thereof capable of accomplishing said reduction; and
recovering said unreacted (4S)-(3,4-dichlorophenyl)-3,4-dihydro-1(2H)-naphthalenone from said resulting mixture.

2. The process as defined in claim 1 wherein said contacting is with said microorganism.
3. The process as defined in claim 2 wherein said microorganism is an intact microorganism.
4. The process as defined in claim 2 wherein said microorganism is a broken cell preparation thereof.
5. The process as defined in claim 2 wherein said microorganism is a dehydrated preparation thereof.
6. The process as defined in claim 5 wherein said dehydrated preparation is an acetone powder enzymatic preparation.
7. The process as defined in claim 3 wherein said intact microorganism comprises washed cells of said intact microorganism.
8. The process as defined in claim 7 wherein said washed cells are immobilized.
9. The process as defined in claim 2 wherein said microorganism is in a culture broth.
10. The process as defined in claim 9 wherein said contacting is by adding said racemic 4-(3,4-dichlorophenyl)-3,4-dihydro-1(2H)-naphthalenone to said culture broth.
11. The process as defined in claim 2 wherein said microorganism is said *Hansenula polymorpha* ATCC No. 26012 or said *Hansenula polymorpha* ATCC No. 74449, or said mutants thereof.
12. The process as defined in claim 9 wherein said microorganism is said *Hansenula polymorpha* ATCC No. 26012 or said *Hansenula polymorpha* ATCC No. 74449, or said mutants thereof.
13. The process as defined in claim 10 wherein said microorganism is said *Hansenula polymorpha* ATCC No. 26012 or said *Hansenula polymorpha* ATCC No. 74449, or said mutants thereof.
14. The process as defined in claim 2 wherein said microorganism is *Absidia coerulea* ATCC No. 20137 or said mutants thereof.
15. The process as defined in claim 1 wherein said unreacted (4S) tetralone is recovered by chromatography or crystallization.
16. The process as defined in claim 1 wherein said contacting is with said enzyme reduction system.
17. The process as defined in claim 16 wherein said enzyme of said enzyme reduction system is immobilized.
18. The process as defined in claim 16 wherein said enzyme reduction system is in a solvent.
19. The process as defined in claim 18 wherein said contacting is by adding said racemic 4-(3,4-dichlorophenyl)-3,4-dihydro-1(2H)-naphthalenone to said solvent.
20. The process as defined in claim 16 wherein said enzyme comprising said enzyme reduction system is obtained from said *Hansenula polymorpha* ATCC No. 26012 or said *Hansenula polymorpha* ATCC No. 74449, or said mutants thereof.
21. The process as defined in claim 16 wherein said enzyme comprising said enzyme reduction system is obtained from said *Absidia coerulea* ATCC No. 20137 or said mutants thereof.
22. The process as defined in claim 2 wherein said enzyme comprising said enzyme reduction system is obtained from said *Monosporium olivaceum* v. *major* ATCC No. 36300 or said mutants thereof.
23. A process for the stereoselective microbial reduction of racemic 4-(3,4-dichlorophenyl)-3,4-dihydro-1(2H)-naphthalenone, where said racemic 4-(3,4-dichlorophenyl)-3,4-dihydro-1(2H)-naphthalenone is a mixture of (4S)-(3,4-dichlorophenyl)-3,4-dihydro-1(2H)-naphthalenone and (4R)-(3,4-dichlorophenyl)-3,4-dihydro-1(2H)-naphthalenone having the formulae

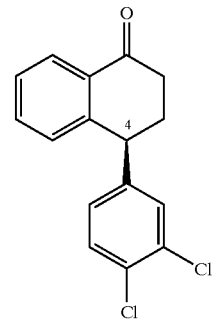

(4S)-(3,4-dichlorophenyl)-3,4-dihydro-1(2H)-naphthalenone, and

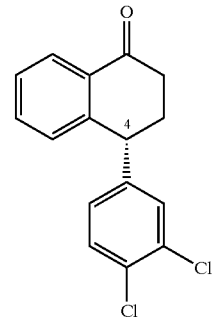

(4R)-(3,4-dichlorophenyl)-3,4-dihydro-1(2H)-naphthalenone, to a mixture of cis and trans tetralols having the formulae:

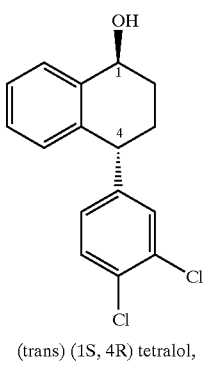
(trans) (1S, 4R) tetralol,

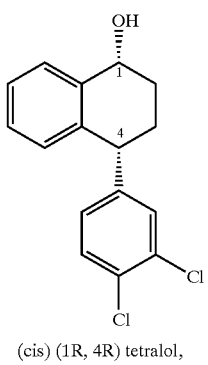
(cis) (1R, 4R) tetralol,

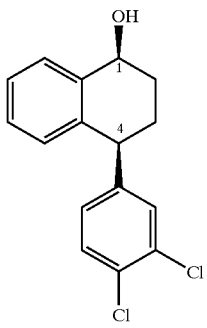
(cis) (1S, 4S) tetralol, and

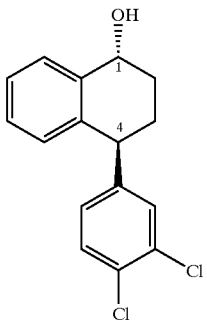
(trans) (1R, 4S) tetralol, to obtain unreacted (4S)-(3,4-dichlorophenyl)-3,4-dihydro-1(2H)-naphthalenone in an ee of greater than 50%, and unreacted (4R)-(3,4-dichlorophenyl)-3,4-dihydro-1(2H)-naphthalenone in an ee of less than 50%, which comprises:
contacting racemic 4-(3,4-dichlorophenyl)-3,4-dihydro-1(2H)-naphthalenone with a microorganism;
incubating the resulting mixture under conditions sufficient to yield said (trans) (1S,4R) tetralol, said (cis) (1R,4R) tetralol, said (trans) (1R,4S) tetralol, and said (cis) (1S,4S) tetralol, and to leave substantially unreacted (4S)-(3,4-dichlorophenyl)-3,4-dihydro-1(2H)-naphthalenone, resulting in unreacted (4S)-(3,4-dichlorophenyl)-3,4-dihydro-1(2H)-naphthalenone being present in ee greater than 50%, and unreacted (4R)-(3,4-dichlorophenyl)-3,4-dihydro-1(2H)-naphthalenone being present in ee less than 50%;
wherein said microorganism is selected from the group consisting of *Hansenula polymorpha* ATCC No. 26012, *Hansenula polymorpha* ATCC No. 74449, *Absidia coerulea* ATCC No. 20137, *Geotrichum candidum* ATCC No. 34614, *Geotrichum candidum* ATCC No. 62401, *Mortierella isabellina* ATCC No. 42613, *Mortierella isabellina* ATCC No. 38063, *Mortierella vinacea* ATCC No. 09515, *Penicillium notatum* ATCC No. 36740, *Blastoschizomyces capitatus* ATCC No. 28575, *Monosporium olivoceum* v. *major* ATCC No. 36300, *Aureobasidium pullulans* ATCC No. 16623, *Debaryomyces polymorphus* ATCC No. 20280, *Saccharomyces cerevisiae* ATCC No. 15248, *Candida schatavii* ATCC No. 24409, *Pichi fabianii* ATCC No. 16755 and *Streptomyces rimosus* ss. *rimosus* ATCC No. 10970; and such mutants thereof capable of accomplishing said reduction; and
recovering said unreacted (4S)-(3,4-dichlorophenyl)-3,4-dihydro-1(2H)-naphthalenone from said resulting mixture.

24. The process as defined in claim 23 wherein said microorganism is in a culture broth.

25. The process as defined in claim 24 wherein said contacting is by adding said racemic 4-(3,4-dichlorophenyl)-3,4-dihydro-1(2H)-naphthalenone to said culture broth.

26. A process for the stereoselective microbial reduction of racemic 4-(3,4-dichlorophenyl)-3,4-dihydro-1(2H)-naphthalenone, where said racemic 4-(3,4-dichlorophenyl)-3,4-dihydro-1(2H)-naphthalenone is a mixture of (4S)-(3,4-dichlorophenyl)-3,4-dihydro-1(2H)-naphthalenone and (4R)-(3,4-dichlorophenyl)-3,4-dihydro-1(2H)-naphthalenone having the formulae

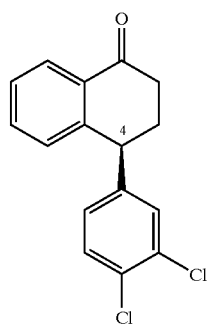

(4S)-(3,4-dichlorophenyl)-3,4-dihydro-1(2H)-naphthalenone, and

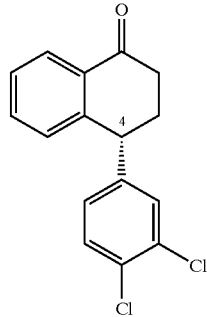

(4R)-(3,4-dichlorophenyl)-3,4-dihydro-1(2H)-naphthalenone, to a mixture of cis and trans tetralols having the formulae:

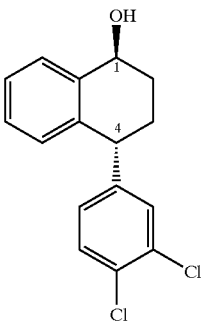
(trans) (1S, 4R) tetralol,

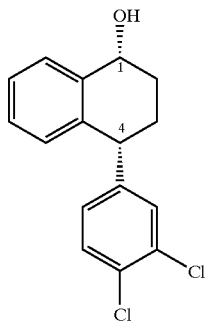
(cis) (1R, 4R) tetralol,

-continued (cis) (1S, 4S) tetralol, and (trans) (1R, 4S) tetralol, to obtain unreacted (4S)-(3,4-dichlorophenyl)-3,4-dihydro-1(2H)-naphthalenone in an ee of greater than 50%, and unreacted (4R)-(3,4-dichlorophenyl)-3,4-dihydro-1(2H)-naphthalenone in an ee of less than 50%, which comprises:
contacting racemic 4-(3,4-dichlorophenyl)-3,4-dihydro-1(2H)-naphthalenone with an enzyme reduction system capable of accomplishing said reduction comprising an enzyme obtained from said microorganism and a co-factor for said enzyme;
incubating the resulting mixture under conditions sufficient to yield said (trans) (1S,4R) tetralol, said (cis) (1R,4R) tetralol, said (trans) (1R,4S) tetralol, and said (cis) (1S,4S) tetralol, and to leave substantially unreacted (4S)-(3,4-dichlorophenyl)-3,4-dihydro-1(2H)-naphthalenone, resulting in unreacted (4S)-(3,4-dichlorophenyl)-3,4-dihydro-1(2H)-naphthalenone being present in ee greater than 50%, and unreacted (4R)-(3,4-dichlorophenyl)-3,4-dihydro-1(2H)-naphthalenone being present in ee less than 50%;
wherein said microorganism is selected from the group consisting of Hansenula polymorpha ATCC No. 26012, Hansenula polymorpha ATCC No. 74449, Absidia coerulea ATCC No. 20137, Geotrichum candidum ATCC No. 3461, Geotrichum candidum ATCC No. 62401, Mortierella isabellina ATCC No. 42613, Mortierella isabellina ATCC No. 38063, Mortierella vinacea ATCC No. 09515, Penicillium notatum ATCC No. 36740, Blastoschizomyces capitatus ATCC No. 28575, Monosporium olivaceum v. major ATCC No. 36300, Aureobasidium pullulans ATCC No. 16623, Debaryomyces polymorphus ATCC No. 20280, Saccharomyces cerevisiae ATCC No. 15248, Candida schatavii ATCC No. 24409, Pichi fabianii ATCC No. 16755 and Streptomyces rimosus ss. rimosus ATCC No. 10970; and such mutants thereof capable of accomplishing said reduction; and
recovering said unreacted (4S)-(3,4-dichlorophenyl)-3,4-dihydro-1(2H)-naphthalenone from said resulting mixture.

27. The process as defined in claim 26 wherein said enzyme reduction system is in a solvent.

28. The process as defined in claim 27 wherein said contacting is by adding said racemic 4-(3,4-dichlorophenyl)-3,4-dihydro-1(2H)-naphthalenone to said solvent.

* * * * *